(12) United States Patent
Chen et al.

(10) Patent No.: US 6,255,470 B1
(45) Date of Patent: *Jul. 3, 2001

(54) ISOLATED NUCLEIC ACID MOLECULE ENCODING AN ESOPHAGEAL CANCER ASSOCIATED ANTIGEN

(75) Inventors: Yao-tseng Chen; Matthew Scanlan; Ali Gure; Lloyd J. Old, all of New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/396,184

(22) Filed: Sep. 14, 1999

Related U.S. Application Data

(62) Division of application No. 09/013,150, filed on Jan. 26, 1998, now Pat. No. 6,069,233, which is a division of application No. 08/725,182, filed on Oct. 3, 1996, now Pat. No. 5,804,381.

(51) Int. Cl.[7] .................... C12N 15/11; C07H 21/04; C12Q 1/68

(52) U.S. Cl. ................... 536/23.1; 536/24.31; 536/24.33; 536/252.1; 536/252.3; 435/6

(58) Field of Search .................... 435/6, 252.1, 252.3; 536/24.3, 24.33, 23.1

(56) References Cited

U.S. PATENT DOCUMENTS 5,804,381 * 9/1998 Chen et al. ............................ 435/6

* cited by examiner

Primary Examiner—Stephanie W. Zitomer
Assistant Examiner—B J Forman
(74) Attorney, Agent, or Firm—Fulbright & Jaworski, LLP

(57) ABSTRACT

The invention relates to the isolation of a nucleic acid molecule which encodes an esophageal cancer associated antigen. Also a part of the invention is the antigen itself, and the uses of the nucleic acid molecule and the antigen.

13 Claims, 3 Drawing Sheets

```
                 ATCCTCGTGGGCCCTGACCTTCTCTCTGAGAGCCGGGCAGAGGCTCCGGAGC
                     Myr   Myr   (P)
                      |     |     |
       M  Q  A  E  G  R  G  T  G  G  S  T  G  D  A  D  G  P  G  G
      CATGCAGGCCGAAGGCCGGGGCACAGGGGGTTCGACGGGCGATGCTGATGGCCCAGGAGG

P  G  I  P  D  G  P  G  G  N  A  G  G  P  G  E  A  G  A  T
      CCCTGGCATTCCTGATGGCCCAGGGGGCAATGCTGGCGGCCCAGGAGAGGCGGGTGCCAC

G  G  R  G  P  R  G  A  G  A  A  R  A  S  G  P  G  G  G  A
      GGGCGGCAGAGGTCCCCGGGGCGCAGGGGCAGCAAGGGCCTCGGGGCCGGGAGGAGGCGC

P  R  G  P  H  G  G  A  A  S  G  L  N  G  C  R  C  G  A
      CCCGCGGGGTCCGCATGGCGGCGCGGCTTCAGGGCTGAATGGATGCTGCAGATGCGGGGC
                                                              (P)
                                                               |
       R  G  P  E  S  R  L  L  E  F  Y  L  A  M  P  F  A  T  P  M
      CAGGGGGCCGGAGAGCCGCCTGCTTGAGTTCTACCTCGCCATGCCTTTCGCGACACCCAT

E  A  E  L  A  R  R  S  L  A  Q  D  A  P  P  L  P  V  P  G
      GGAAGCAGAGCTGGCCCGCAGGAGCCTGGCCCAGGATGCCCCACCGCTTCCCGTGCCAGG (P)           (P)
                                           |             |
       V  L  L  K  E  F  T  V  S  G  N  I  L  T  I  R  L  T  A  A
      GGTGCTTCTGAAGGAGTTCACTGTGTCCGGCAACATACTGACTATCCGACTGACTGCTGC

D  H  R  Q  L  Q  L  S  I  S  S  C  L  Q  Q  L  S  L  L  M
      AGACCACCGCCAACTGCAGCTCTCCATCAGCTCCTGTCTCCAGCAGCTTTCCCTGTTGAT

W  I  T  Q  C  F  L  P  V  F  L  A  Q  P  P  S  G  Q  R  R
      GTGGATCACGCAGTGCTTTCTGCCCGTGTTTTTGGCTCAGCCTCCCTCAGGGCAGAGGCG

CTAAGCCCAGCCTGGCGCCCCTTCCTAGGTCATGCCTCCTCCCCTAGGGAATGGTCCCAG
       *
      CACGAGTGGCCAGTTCATTGTGGGGGCCTGATTGTTTGTCGCTGGAGGAGGACGGCTTAC
      ATGTTTGTTTCTGTAGAAAATAAAACTGAGCTACGAAAAA
```

ISOLATED NUCLEIC ACID MOLECULE ENCODING AN ESOPHAGEAL CANCER ASSOCIATED ANTIGEN

RELATED APPLICATIONS.

This application-is a divisional of Ser. No. 09/013,150, filed Jan. 26, 1998, now U.S. Pat. No. 6,069,233 which is a divisional of Ser. No. 08/725,182, filed Oct. 3, 1996, now U.S. Pat. No. 5,804,381.

FIELD OF THE INVENTION

This invention relates to an antigen associated with esophageal cancer, and the nucleic acid molecule encoding it, as well as the uses of these.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding molecule to express the desired molecule.

To date, two strategies have been employed for the detection of such antigens, in e.g., human tumors. These will be referred to as the genetic approach and the biochemical approach. The genetic approach is exemplified by, e.g., dePlaen et al., Proc. Natl. Sci. U.S.A. 85: 2275 (1988), incorporated by reference. In this approach, several hundred pools of plasmids of a cDNA library obtained from a tumor are transfected into recipient cells, such as COS cells, or into antigen-negative variants of tumor cell lines which are tested for the expression of the specific antigen. The biochemical approach, exemplified by, e.g., Kawakami, et al., Nature 369: 69 (1994) incorporated by reference, is based on acidic elution of peptides which have bound to MHC-class I molecules of tumor cells, followed by reversed-phase high performance liquid chromatography (HPLC). Antigenic peptides are identified after they bind to empty MHC-class I molecules of mutant cell lines, defective in antigen processing, and induce specific reactions with cytotoxic T-lymphocytes. These reactions include induction of CTL proliferation, TNF release, and lysis of target cells, measurable in an MTT assay, or a $^{51}Cr$ release assay.

These two approaches to the molecular definition of antigens have the following disadvantages: first, they are enormously cumbersome, time-consuming and expensive; second, they depend on the establishment of cytotoxic T cell lines (CTLs) with predefined specificity; and third, their relevance in vivo for the course of the pathology of disease in question has not been proven, as the respective CTLs can be obtained not only from patients with the respective disease, but also from healthy individuals, depending on their T cell repertoire.

The problems inherent to the two known approaches for the identification and molecular definition of antigens is best demonstrated by the fact that both methods have, so far, succeeded in defining only very few new antigens in human tumors. See, e.g., van der Bruggen et al., Science 254:1643–1647 (1991); Brichard et al., J. Exp. Med. 178: 489–495 (1993); Coulie, et al., J. Exp. Med. 180: 35–42 (1994); Kawakami, et al., Proc. Natl. Acad. Sci. U.S.A. 91: 3515–3519 (1994).

Further, the methodologies described rely on the availability of established, permanent cell lines of the cancer type under consideration. It is very difficult to establish cell lines from certain cancer types, as is shown by, e.g., Oettgen, et al., Immunol. Allerg. Clin. North. Am. 10: 607–637 (1990). It is also known that some epithelial cell type cancers are poorly susceptible to CTLs in vitro, precluding routine analysis. These problems have stimulated the art to develop additional methodologies for identifying cancer associated antigens.

One key methodology is described by Sahin, et al., Proc. Natl. Acad. Sci. USA 92: 11810–11913 (1995), incorporated by reference. Also, see U.S. patent applications Ser. No. 08/580,980, and application Ser. No. 08/479,328, filed on Jun. 7, 1995 and Jan. 3, 1996, respectively. All three of these references are incorporated by reference. To summarize, the method involves the expression of cDNA libraries in a prokaryotic host. (The libraries are secured from a tumor sample). The expressed libraries are then immnoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patent applications and Sahin, et al., supra, as well as Crew, et al., EMBO J 144:2333–2340 (1995).

The SEREX methodology has been applied to esophageal cancer samples, and an esophageal cancer associated antigen has now been identified, and its encoding nucleic acid molecule isolated and cloned. This, inter alia, is the subject of the invention, which is described in more detail in the disclosure which follows.

BRIEF DESCRIPTION OF THE FIGURES

FIG. 3 shows potential sites for modification of the deduced amino acid sequence of NY-ESO-1.

DETAILED DESCRIPTION OF PREFERRED EMBODIMENTS

EXAMPLE 1

Figure 1A:
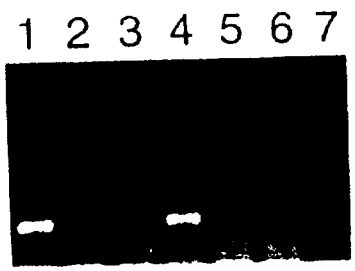
FIGS. 1A and 1B show the expression pattern of RNA for the NY-ESO-1 antigen, in various tissue types.
Figure 1B:
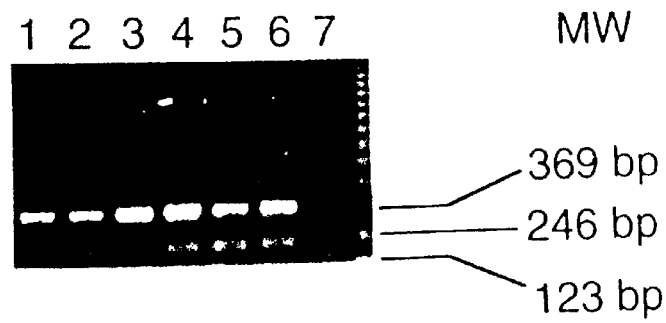
Figure 2:
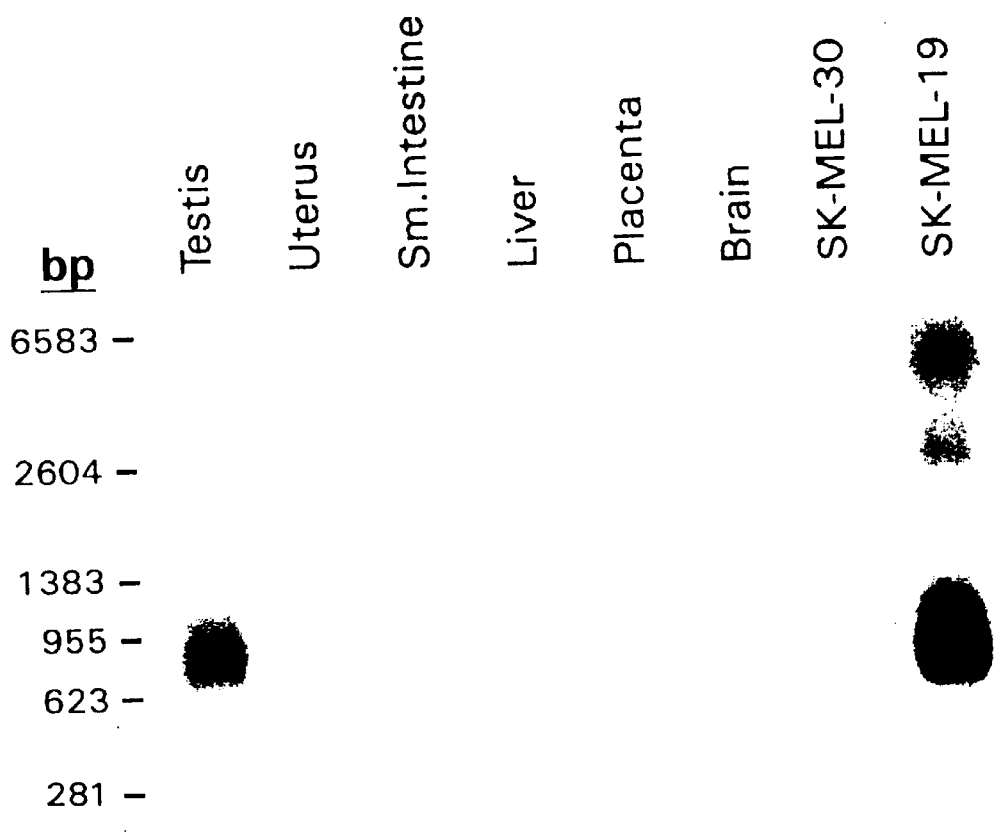
FIG. 2 shows Northern Blot analysis of NY-ESO-1 mRNA, which was found in testis and cell line SK-MEL-19, but not in various other cell and tissue samples.
Figure 4:
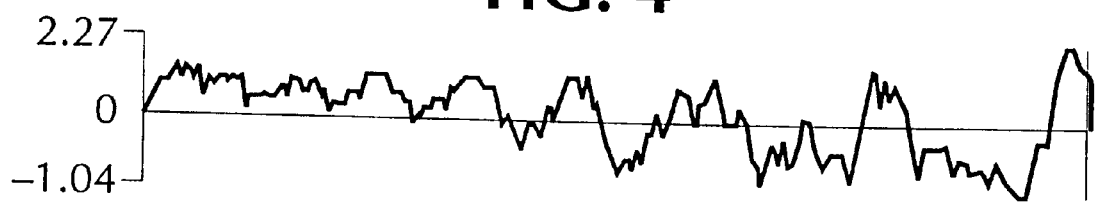
FIG. 4 is a hydrophilicity plot of NY-ESO-1, showing hydrophilic domains in the amino terminus and a long, hydrophobic stretch close to the carboxyl end.

Total RNA was extracted from a snap frozen specimen of well to moderately differentiated squamous cell cancer of the esophagus, using well known methods. See, e.g., Chomzynski, J. Analyt. Biochem. 162: 156–159 (1987), for one such method. This RNA was used to prepare a cDNA library which was then transfected into λZAP phage vectors, in accordance with the manufacturer's instruction. The λZAP library was then transfected into E. coli, yielding $1.6 \times 10^6$ primary isolates.

The SEREX methodology of Sahin, et al., Proc. Natl. Acad. Sci. USA 92: 11810–11813 (1995), incorporated by reference, was then used. In brief, autologous serum was stripped of antibodies against molecules which are endogenous to E. coli by combining the serum with lysates of E. coli transfected with phage λZAP which did not contain the cDNA clones from the esophageal cancer cells.

The depleted serum was then diluted, and mixed with nitrocellulose membranes containing phage plaques. The plaques were incubated overnight, at room temperature. Washing followed, and then the filters were incubated with alkaline phosphatase conjugated goat anti human FCγ secondary antibodies, and reactive phage plaques were visualized by incubating with 5-bromo-4-chloro-indolyl phosphate and nitroblue tetrazolium. A total of 13 positive clones were found.

EXAMPLE 2

Following identification, the reactive clones were subcloned to monoclonality via dilution cloning and testing with human serum. These clones were then purified, excised in vitro, and converted into pBK-CMV plasmid forms, using the manufacturer's instructions. The inserted DNA was then evaluated using EcoRI-XbaI restriction mapping to determine different inserts. Eight different inserts were identified, ranging in size from about 500 to about 1.3 kilobase pairs. The clones were sequenced using an ABI PRISM automated sequencer.

Table 1 summarizes the results. One gene was represented by four overlapping clones, a second by three overlapping clones, and the remaining six by one clone only.

A homology search revealed that the clones referred to as NY-ESO-2, 3, 6, 7 were already known. See Elisei, et al., J. Endocrin. Invest. 16: 533–540 (1993); Spritz, et al., Nucl. Acids Res. 15: 10373–10391 (1987); Rabbits, et al., Nature Genetics 4: 175–180 (1993); Crozat, et al., Nature 363: 640–644 (1993); GenBank H18368 and D25606. Two of the clones (NY-ESO-3 and NY-ESO-6), have previously been shown to be expressed in various normal human tissues. No evidence of lineage restriction has been found. NY-ESO-6 (cDNA), appears to be the 3'-untranslated portion of the FUS/TLS gene. In experiments not reported here, sequencing and Southern Blot analysis of NY-ESO-6 showed no evidence of translocation or point mutations in the cancer. Four of the clones, i.e., NY-ESO-1, 4, 5 and 8 showed no strong homology to sequences in the databases examined, and were thus studied further.

TABLE 1

Genes isolated from esophageal cancer library by immunoscreening with autologous serum

| GENE | CLONE# | size | DNA databank | Comments* |
|---|---|---|---|---|
| NY-ESO-1 | E1-5b | 679 bp | No strong homology | expressed in testis and ovary |
|  | E1-114b | 614 bp |  |  |
|  | E1-153c | 670 bp |  |  |
|  | E1-50 | 679 bp |  |  |
| NY-ESO-2 | E1-71a | 605 bp | U1 small nuclear RNP 1 homolog | cloned by Ab screening (thyroiditis patient) |
|  | E1-140 | 874 bp |  |  |
|  | E1-31 | 750 bp |  |  |
| NY-ESO-3 | E1-141b | 517 bp | Colon 3' direct MboI cDNA; Adult brain cDNA | (dbj D25606, gb H18638) unpublished |
| NY-ESO-4 | E1A-10c | 400 bp | No strong homology | ubiquitous expression in normal tissues |
| NY-ESO-5 | E1A-54 | 670 bp | No strong homology | expressed in normal esophagus |
| NY-ESO-6 | E1B-9b | ≈1.2 kb | Human fus mRNA | translocated in liposarcoma t(12;16) |
| NY-ESO-7 | E1B-20f | ≈1.0 kb | human U1-70k sn RNP | different from NY-ESO-2 (embl HSU17052, gbM22636) |
| NY-ESO-8 | E1B-20g | ≈1.3 kb | No strong homology | ubiquitous expression in normal tissues |

EXAMPLE 3

Studies were carried out to evaluate mRNA expression of the NY-ESO 1, 4, 5 and 8 clones. To do this, specific oligonucleotide primers were designed for each sequence, such that cDNA segments of 300–400 base pairs could be amplified, and so that the primer melting temperature would be in the range of 65–70° C. Reverse Transcription-PCR was then carried out using commercially available materials and standard protocols. A variety of normal and tumor cell types were tested. The clones NY-ESO-4 and NY-ESO-8 were ubiquitous, and were not studied further. NY-ESO-5 showed high level expression in the original tumor, and in normal esophageal tissue, suggesting that it was a differentiation marker.

NY-ESO-1 was found to be expressed in tumor mRNA and in testis, but not normal colon, kidney, liver or brain tissue. This pattern of expression is consistent with other tumor rejection antigen precursors.

EXAMPLE 4

The RT-PCR assay set forth supra was carried out for NY-ESO-1 over a much more complete set of normal and tumor tissues. Tables 2, 3 and 4 show these results. In brief, NY-ESO-1 was found to be highly expressed in normal testis and ovary cells. Small amounts of RT-PCR production were found in normal uterine myometrium, and not endometrium, but the positive showing was not consistent. Squamous epithelium of various cell types, including normal esophagus and skin, were also negative.

When tumors of unrelated cell lineage were tested, 2 of 11 melanomas cell lines showed strong expression, as did 16 of 67 melanoma specimens, 6 of 33 breast cancer specimens and 4 of 4 bladder cancer. There was sporadic expression in other tumor types.

TABLE 2 mRNA distribution of NY-ESO-1 in normal tissues:

| Tissue | NY-ESO-1 mRNA |
| --- | --- |
| esophagus | − |
| brain* | − |
| fetal brain | − |
| heart | − |
| lung | − |
| liver | − |
| spleen | − |
| kidney | − |
| stomach | − |
| small intestine | − |
| colon | − |
| rectum | − |
| breast | − |
| skin | − |
| thyroid | − |
| adrenal | − |
| pancreas | − |
| vesicula testis | − |
| placenta | − |
| thymus | − |
| lymph node | − |
| tonsil | − |
| PBL | − |
| PBL, activated# | − |
| melanocytes | − |
| uterus | +/−** |
| testis | + |
| ovary | + |

*tissues from several different parts were tested.
with IL-2 and PHA
**weakly positive in some specimens, negative by Northern blot

TABLE 3 mRNA distribution of NY-ESO-1 in melanoma and breast cancer cell lines:

| Cell line | NY-ESO-1 mRNA |
| --- | --- |
| MZ2-Mel3.1 | − |
| MZ2-Mel2.2 | − |
| SK-MEL-13 | − |
| SK-MEL-19 | + |
| SK-MEL-23 | − |
| SK-MEL-29 | − |

TABLE 3-continued mRNA distribution of NY-ESO-1 in melanoma and breast cancer cell lines:

| Cell line | NY-ESO-1 mRNA |
| --- | --- |
| SK MEL-30 | − |
| SK-MEL-31 | − |
| SK-MEL-33 | − |
| SK-MEL-37 | + |
| SK-MEL-179 | − |
| SK-BR-3 | − |
| SK-BR-5 | − |
| 734B | − |
| MDA-MB-231 | − |

TABLE 4 mRNA distribution of NY-ESO-1 in tumor tissues

| Tumor type | NY-ESO-1 mRNA (positive/total) |
| --- | --- |
| melanoma | 16/67 (and 7 weak +) |
| breast cancer | 6/33 (and 4 weak +) |
| prostate cancer | 3/16 (and 1 weak +) |
| colon cancer | 0/16 |
| glioma | 0/15 |
| gastric cancer | 0/12 |
| renal cancer | 0/10 |
| lymphoma | 0/10 |
| lung cancer | 2/12 |
| hepatocellular carcinoma | 2/7 |
| ovarian cancer | 2/8 |
| thyroid cancer | 2/5 |
| bladder cancer | 4/4 |
| Burkitt's lymphoma | 0/2 (1 weak +) |
| basal cell carcinoma | 0/2 |
| leiomyosarcoma | 0/2 |
| sarcoma | 0/2 |
| pancreatic cancer | 0/2 |
| seminoma | 0/1 |
| spinal cord tumor | 0/1 |

EXAMPLE 5

Northern blot analysis was then carried out to investigate the size of the NY-ESO-1 transcript, and to confirm tissue expression patterns. The methodology of Ausubel, et al., *Current Protocols In Molecular Biology* (John Wiley & Sons, 1995) was used. To be specific, 20 ug of total RNA per lane were dissolved in a formamide and formaldehyde containing buffer, heated to 65° C., and then separated on a 1.2% agarose gel, with 3% formaldehyde, followed by transfer to nitrocellulose paper. Hybridization was then carried out using a $^{32}$P labelled probe, followed by high stringency washing. The final wash was at 0.1×SSC, 0.1% SDS, 60° C., for 15 minutes.

RNA from testis, and a melanoma cell line (SK-MEL-19) which had been positive for NY-ESO-1 in the prior assays, showed an RNA transcript of about 0.8–0.9 kb. An esophageal carcinoma specimen showed a smear in the 0.4–0.9 kb range, reflecting partial degradation. RNA from additional tissues or cell lines tested showed no transcript.

To get cDNA encoding the full transcript, the esophageal cDNA library was rescreened, using plaque hybridization, and the original cDNA clone as the hybridization probe. When 3×10$^5$ clones were screened, six positives were found. The three longest clones were sequenced. Analysis of open reading frames showed that all three contained the entire coding region, and 5'-untranslated regions of variable size.

The longest clone, 755 base pairs in length, (excluding polyA), contains a 543 base pair coding region, together with 53 untranslated and 151 untranslated base pairs at the 3'-end. See SEQ ID NO: 1 (also, FIG. 3).

The long ORF indicated that the deduced sequence of NY-ESO-1 protein is 180 amino acids. The single immunopositive clone contained a sequence encoding 173 of these. Deduced molecular mass is 17,995 daltons.

Analysis shows that there is an abundance of glycine residues in the N-terminal portion (30 of the first 80, 4 in the remaining 100). Hydrophilicity analysis indicated that there were hydrophilic antigenic sequences in the N-terminal half of the molecule, with alternating hydrophobic and hydrophilic sequences, ending with a long, C-terminal hydrophobic tail (amino acids 152–172), followed by a short hydrophilic tail. This pattern suggests a transmembrane domain. There are several potential N-myristorylation sites, 3 phosphorylation sites, and no evidence of N-glycosylation sites.

The foregoing examples describe the isolation of a nucleic acid molecule which encodes an esophageal cancer associated antigen. "Associated" is used herein because while it is clear that the relevant molecule was expressed by esophageal cancer, not all cancer cells and types could be tested. Hence, the molecule may be expressed on other tumor cells.

The invention relates to those nucleic acid molecules which encode antigens as described, and which hybridize to reference sequence SEQ ID NO: 1 under stringent conditions. "Stringent conditions" as used herein refers to conditions such as those specified in U.S. Pat. No. 5,342,774, i.e., 18 hours of hybridization at 65° C., followed by four one hour washes at 2×SSC, 0.1% SDS, and a final wash at 0.2×SSC, more preferably 0.1×SSC, 0.1% SDS for 30 minutes, as well as alternate conditions which afford the same level of stringency, and more stringent conditions.

Also a part of the invention are expression vectors which incorporate the nucleic acid molecules of the invention, in operable linkage (i.e., "operably linked") to a promoter. Construction of such vectors is well within the skill of the art, as is the transformation or transfection of cells, to produce eukaryotic cell lines, or prokaryotic cell strains which encode the molecule of interest. Exemplary of the host cells which can be employed in this fashion are COS cells, CHO cells, yeast cells, insect cells (e.g., *Spodoptera frugiperda*), NIH 3T3 cells, and so forth. Prokaryotic cells, such as *E. coli* and other bacteria may also be used.

Also a part of the invention is the antigen described herein, both in original peptide form and in post translational modified form. The molecule is large enough to be antigenic without any posttranslational modification, and hence it is useful as an immunogen, when combined with an adjuvant (or without it), in both precursor and post-translationally modified forms. Also a part of the invention are antibodies against this antigen, be these polyclonal, monoclonal, reactive fragments, such as Fab, F(ab)$_2$' and other fragments, as well as chimeras, humanized antibodies, recombinantly produced antibodies, and so forth.

As is clear from the disclosure, one may use the proteins and nucleic acid molecules of the invention diagnostically. The SEREX methodology discussed herein is premised on an immune response to a pathology associated antigen. Hence, one may assay for the relevant pathology via, e.g., testing a body fluid sample of a subject, such as serum, for reactivity with the antigen per se. Reactivity would be deemed indicative of possible presence of the pathology so, too, could one assay for the expression of the antigen via any of the standard nucleic acid hybridization assays which are well known to the art, and need not be elaborated upon herein.

Analysis of SEQ ID NO: 1 will show that there are 5' and 3' non coding regions presented therein. The invention relates to those isolated nucleic acid molecules which contain at least the coding segment, i.e., nucleotides 62–600, and which may contain any or all of nucleotides 1–61 and/or 601–755 of SEQ ID NO: 1.

Other features and applications of the invention will be clear to the skilled artisan, and need not be set forth herein.

The terms and expression which have been employed are used as terms of description and not of limitation, and there is no intention in the use of such terms and expression of excluding any equivalents of the features shown and described or portions thereof, it being recognized that various modifications are possible within the scope of the invention.

We claim:

1. An isolated cDNA molecule which encodes a protein which, when expressed by a human, elicits a humoral response by said human against said protein, said protein being a tumor associated antigen, wherein the complementary sequence of said isolated cDNA molecule hybridizes fully, under stringent conditions, to the cDNA molecule consisting of nucleotides 54–600 of SEQ ID NO: 1.

2. The isolated cDNA of claim 1, consisting of nucleotides 54–600 of SEQ ID NO: 1.

3. The isolated cDNA of claim 1, consisting of any where from nucleotide 1 through nucleotide 755 of SEQ ID NO: 1, with the proviso that said isolated cDNA contains at least nucleotides 54–600 of SEQ ID NO: 1.

4. Expression vector comprising the isolated cDNA of claim 1, operably linked to a promoter.

5. Expression vector comprising the isolated nucleic acid molecule of claim 3, operably linked to a promoter.

6. Eukaryotic cell line or prokaryotic cell strain, transformed or transfected with the expression vector of claim 4.

7. Eukaryotic cell line or prokaryotic cell strain, transformed or transfected with the expression vector of claim 5.

8. Prokaryotic cell strain or eukaryotic cell line, transformed or transfected with the isolated cDNA of claim 1.

9. The procaryotic cell strain of claim 8, comprising *E. coli*.

10. The eukaryotic cell line of claim 8, wherein said eukaryotic cell line comprises COS cells, CHO cells, yeast cells, insect cells or NIH 3T3 cells.

11. Procaryotic cell strain or eukaryotic cell line transformed or transfected with the nucleic acid expression vector of claim 4.

12. The procaryotic cell strain of claim 11, comprising *E. coli*.

13. The eukaryotic cell line of claim 11, comprising COS cells, CHO cells, yeast cells, insect cells or NIH 3T3 cells.

* * * * *

UNITED STATES PATENT AND TRADEMARK OFFICE
CERTIFICATE OF CORRECTION

PATENT NO. : 6,255,470 B1
DATED : July 3, 2001
INVENTOR(S) : Chen et al.

It is certified that error appears in the above-identified patent and that said Letters Patent is hereby corrected as shown below:

<u>Title page,</u>
Item [73], Assignee, insert -- Cornell Research Foundation, Ithaca, NY, Ludwig Institute for Career Research, New York, NY (US) --

Signed and Sealed this

Second Day of July, 2002

*Attest:*

JAMES E. ROGAN
*Attesting Officer*     *Director of the United States Patent and Trademark Office*

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
        (A) LENGTH: 752 base pairs
        (B) TYPE: nucleic acid
        (C) STRANDEDNESS: double
        (D) TOPOLOGY: linear (xi) SEQUENCE DESCRIPTION: SEQ ID NO: 1:

```
ATCCTCGTGG GCCCTGACCT TCTCTCTGAG AGCCGGGCAG AGGCTCCGGA GCC            53

ATG CAG GCC GAA GGC CGG GGC ACA GGG GGT TCG ACG GGC GAT GCT           98
Met Gln Ala Glu Gly Arg Gly Thr Gly Gly Ser Thr Gly Asp Ala
```

-continued

|  |  |  |  |  |  |  |  |  |  |  |  |  |
|---|---|---|---|---|---|---|---|---|---|---|---|---|
| | | | 5 | | | | 10 | | | | 15 | |
| GAT | GGC | CCA | GGA | GGC | CCT | GGC | ATT | CCT | GAT | GGC | CCA | GGG | GGC | AAT | 143 |
| Asp | Gly | Pro | Gly | Gly | Pro | Gly | Ile | Pro | Asp | Gly | Pro | Gly | Gly | Asn | |
| | | | | 20 | | | | | 25 | | | | | 30 | |
| GCT | GGC | GGC | CCA | GGA | GAG | GCG | GGT | GCC | ACG | GGC | GGC | AGA | GGT | CCC | 188 |
| Ala | Gly | Gly | Pro | Gly | Glu | Ala | Gly | Ala | Thr | Gly | Gly | Arg | Aly | Pro | |
| | | | | 35 | | | | | 40 | | | | | 45 | |
| CGG | GGC | GCA | GGG | GCA | GCA | AGG | GCC | TCG | GGG | CCG | GGA | GGA | GGC | GCC | 233 |
| Arg | Gly | Ala | Gly | Ala | Ala | Arg | Ala | Ser | Gly | Pro | Gly | Gly | Gly | Ala | |
| | | | | 50 | | | | | 55 | | | | | 60 | |
| CCG | CGG | GGT | CCG | CAT | GGC | GGC | GCG | GCT | TCA | GGG | CTG | AAT | GGA | TGC | 278 |
| Pro | Arg | Gly | Pro | His | Gly | Gly | Ala | Ala | Ser | Gly | Leu | Asn | Gly | Cys | |
| | | | | 65 | | | | | 70 | | | | | 75 | |
| TGC | AGA | TGC | GGG | GCC | AGG | GGG | CCG | GAG | AGC | CGC | CTG | CTT | GAG | TTC | 323 |
| Cys | Arg | Cys | Gly | Ala | Arg | Gly | Pro | Glu | Ser | Arg | Leu | Leu | Glu | Phe | |
| | | | | 80 | | | | | 85 | | | | | 90 | |
| TAC | CTC | GCC | ATG | CCT | TTC | GCG | ACA | CCC | ATG | GAA | GCA | GAG | CTG | GCC | 368 |
| Tyr | Leu | Ala | Met | Pro | Phe | Ala | Thr | Pro | Met | Glu | Ala | Glu | Leu | Ala | |
| | | | | 95 | | | | | 100 | | | | | 105 | |
| CGC | AGG | AGC | CTG | GCC | CAG | GAT | GCC | CCA | CCG | CTT | CCC | GTG | CCA | GGG | 413 |
| Arg | Arg | Ser | Leu | Ala | Gln | Asp | Ala | Pro | Pro | Leu | Pro | Val | Pro | Gly | |
| | | | | 110 | | | | | 115 | | | | | 120 | |
| GTG | CTT | CTG | AAG | GAG | TTC | ACT | GTG | TCC | GGC | AAC | ATA | CTG | ACT | ATC | 458 |
| Val | Leu | Leu | Lys | Glu | Phe | Thr | Val | Ser | Gly | Asn | Ile | Leu | Thr | Ile | |
| | | | | 125 | | | | | 130 | | | | | 135 | |
| CGA | CTG | ACT | GCT | GCA | GAC | CAC | CGC | CAA | CTG | CAG | CTC | TCC | ATC | AGC | 503 |
| Arg | Leu | Thr | Ala | Ala | Asp | His | Arg | Gln | Leu | Gln | Leu | Ser | Ile | Ser | |
| | | | | 140 | | | | | 145 | | | | | 150 | |
| TCC | TGT | CTC | CAG | CAG | CTT | TCC | CTG | TTG | ATG | TGG | ATC | ACG | CAG | TGC | 548 |
| Ser | Cys | Leu | Gln | Gln | Leu | Ser | Leu | Leu | Met | Trp | Ile | Thr | Gln | Cys | |
| | | | | 155 | | | | | 160 | | | | | 165 | |
| TTT | CTG | CCC | GTG | TTT | TTG | GCT | CAG | CCT | CCC | TCA | GGG | CAG | AGG | CGC | 593 |
| Phe | Leu | Pro | Val | Phe | Leu | Ala | Gln | Pro | Pro | Ser | Gly | Gln | Arg | Arg | |
| | | | | 170 | | | | | 175 | | | | | 180 | |

TAA GCCCAGCCTG GCGCCCCTTC CTAGGTCATG CCTCCTCCCC TAGGGAATGG    646

TCCCAGCACG AGTGGCCAGT TCATTGTGGG GGCCTGATTG TTTGTCGCTG GAGGAGGAC    706

GCTTACATGT TTGTTTCTGT AGAAAATAAA ACTGAGCTAC GAAAAA    752